(12) United States Patent
Kono et al.

(10) Patent No.: US 10,459,192 B2
(45) Date of Patent: Oct. 29, 2019

(54) DRIVING UNIT, OPTICAL UNIT, IMAGING APPARATUS, AND ENDOSCOPE

(71) Applicant: OLYMPUS CORPORATION, Tokyo (JP)

(72) Inventors: Shinya Kono, Tokyo (JP); Takehiko Iguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 257 days.

(21) Appl. No.: 15/219,411

(22) Filed: Jul. 26, 2016

(65) Prior Publication Data

US 2016/0334599 A1    Nov. 17, 2016

Related U.S. Application Data

(63) Continuation of application No. PCT/JP2014/072901, filed on Sep. 1, 2014.

(30) Foreign Application Priority Data

Jan. 28, 2014    (JP) ................. 2014-013274

(51) Int. Cl.
*G02B 7/00*    (2006.01)
*G02B 7/10*    (2006.01)
(Continued)

(52) U.S. Cl.
CPC .......... *G02B 7/102* (2013.01); *A61B 1/00096* (2013.01); *A61B 1/00188* (2013.01);
(Continued)

(58) Field of Classification Search
CPC .................................................. G02B 7/102
(Continued)

(56) References Cited

U.S. PATENT DOCUMENTS 5,876,327 A * 3/1999 Tsuyuki ............. A61B 1/00096
600/112
6,853,808 B1    2/2005 Yasuda et al.
(Continued)

FOREIGN PATENT DOCUMENTS

CN    1465996 A    1/2004
CN    101135763 A    3/2008
(Continued)

OTHER PUBLICATIONS

Extended Supplementary European Search Report dated Jul. 21, 2017 in European Patent Application No. 14 88 0520.3.
(Continued)

*Primary Examiner* — Dave Czekaj
*Assistant Examiner* — Shanika M Brumfield
(74) *Attorney, Agent, or Firm* — Scully, Scott, Murphy & Presser, P.C.

(57) ABSTRACT

A driving unit includes
a tubular fixed part with a given axis as center,
a movable part located inside the fixed part and having the axis as center,
a front frame part attached to the fixed part and including at least a magnetic material, and
a voice coil motor capable of moving the movable part relatively with respect to the fixed part in the axial direction by a coil wound around an outer circumference of the fixed part and a magnet located in the movable part, wherein the magnet of the movable part is biased by the magnetic material, and an axial width of the coil is longer than an axial width of the magnet.

9 Claims, 12 Drawing Sheets

(51) Int. Cl.
*G02B 7/08* (2006.01)
*H02K 33/16* (2006.01)
*A61B 1/00* (2006.01)
*G02B 23/24* (2006.01)
*H04N 5/225* (2006.01)
*G03B 3/10* (2006.01)
*G03B 5/00* (2006.01)

(52) U.S. Cl.
CPC ........... *G02B 7/08* (2013.01); *G02B 23/2423* (2013.01); *G02B 23/2438* (2013.01); *G03B 3/10* (2013.01); *G03B 5/00* (2013.01); *H02K 33/16* (2013.01); *H04N 5/2257* (2013.01); *A61B 1/00158* (2013.01); *G03B 2205/0046* (2013.01); *G03B 2205/0069* (2013.01); *H04N 2005/2255* (2013.01)

(58) Field of Classification Search
USPC .......................................................... 348/65
See application file for complete search history.

(56) References Cited

U.S. PATENT DOCUMENTS

| | | | |
|---|---|---|---|
| 7,630,151 B2 | 12/2009 | Fujita et al. | |
| 7,777,978 B2 | 8/2010 | Sato | |
| 8,803,957 B2 | 8/2014 | Makiyama et al. | |
| 2012/0002102 A1* | 1/2012 | Sekimoto | G02B 7/022 348/374 |
| 2013/0314517 A1* | 11/2013 | Makiyama | A61B 1/045 348/65 |

FOREIGN PATENT DOCUMENTS

| | | | | |
|---|---|---|---|---|
| JP | H10-133126 A | | 5/1998 | |
| JP | 2004-280039 A | | 10/2004 | |
| JP | 2005-064887 A | | 3/2005 | |
| JP | 2005-308780 A | | 11/2005 | |
| JP | 2005308780 A | * | 11/2005 | |
| JP | 2005308780 A | * | 11/2005 | |
| JP | 2006-276565 A | | 10/2006 | |
| JP | 2007-041616 A | | 2/2007 | |
| JP | 2007041616 A | * | 2/2007 | |
| JP | 2007041616 A | * | 2/2007 | |
| JP | 2007-174222 A | | 7/2007 | |
| JP | 2009069611 A | * | 4/2009 | ............ G02B 7/022 |
| JP | 2009-160276 A | | 7/2009 | |
| JP | 4804325 B2 | | 11/2011 | |
| JP | 5274733 A | | 8/2013 | |
| WO | WO 2005/066681 A1 | | 7/2005 | |

OTHER PUBLICATIONS

International Search Report dated Nov. 4, 2014 issued in PCT/JP2014/072901.

* cited by examiner

DRIVING UNIT, OPTICAL UNIT, IMAGING APPARATUS, AND ENDOSCOPE

CROSS-REFERENCE TO RELATED APPLICATIONS

This application is a continuation claiming priority on the basis of Japan Patent Application No. 2014-013274 applied in Japan on Jan. 28, 2014 and based on PCT/JP2014/072901 filed on Sep. 1, 2014. The contents of both the PCT application and the Japan Application are incorporated herein by reference.

BACKGROUND OF THE INVENTION AND RELATED ART STATEMENT

The present invention relates to a driving unit, an optical unit, an imaging apparatus, and an endoscope, in which a voice coil motor is used to drive a movable part for advanceable and retractable movement.

So far a voice coil motor (VCM) have been used every so often in the form of a driving force for moving a moving unit, and with a recent progress of diagnostic technology it has been desired to make optical characteristics such as focus and the angle of field variable upon endoscopic viewing. An endoscope capable of normal viewing and magnifying viewing includes a moving means for axial movement of a moving unit including an optical lens into an imaging apparatus built in an insert part. The VCM is sometimes used as such an endoscopic moving means. In that case, normal viewing is implemented when the moving unit is moved on the wide-angle end side while magnifying viewing is implemented as the moving unit is moved toward the telephoto end side. The endoscope is more frequently used in the normal viewing mode, and when the moving unit is held in abutment against the wide-end surface by the voice coil motor, there has been the need for feeding electric current constantly through the voice coil motor so as to take hold of the position of the moving unit. This has often incurred increased power consumption of the voice coil motor, resulting in a temperature rise due to heat generated from the coil. In order to decrease electric current through the coil there has been a method proposed in the art, in which biasing force is generated by making use of magnetic flux leakage from a magnetic circuit (see Japanese Patent No. 4804325).

SUMMARY OF INVENTION

According to one aspect of the invention, there is a driving unit provided, which includes a tubular fixed part with a given axis as center, a tubular movable part located inside the fixed part with the axis as center, a front frame part attached to one end side of the fixed part and including at least a magnetic material, and a voice coil motor that is capable of moving the movable part relatively with respect to the fixed part in a direction of the axis by a coil located in the fixed part and a magnet located in the movable part, wherein the magnet in the movable part is biased by the magnetic material during no passage of electric current through the coil.

According to another aspect of the invention, there is an imaging apparatus provided, which includes the optical unit and a back frame part attached to other end side of the fixed part, wherein the back frame part includes a back lens group on which light passing through the optical member is incident and an imaging device on which light passing through the back lens group is incident.

According to yet another aspect of the invention, there is an endoscope provided, which includes the imaging apparatus.

DESCRIPTION OF EMBODIMENTS

The driving unit according to the embodiment described herein is now explained.

Figure 1:
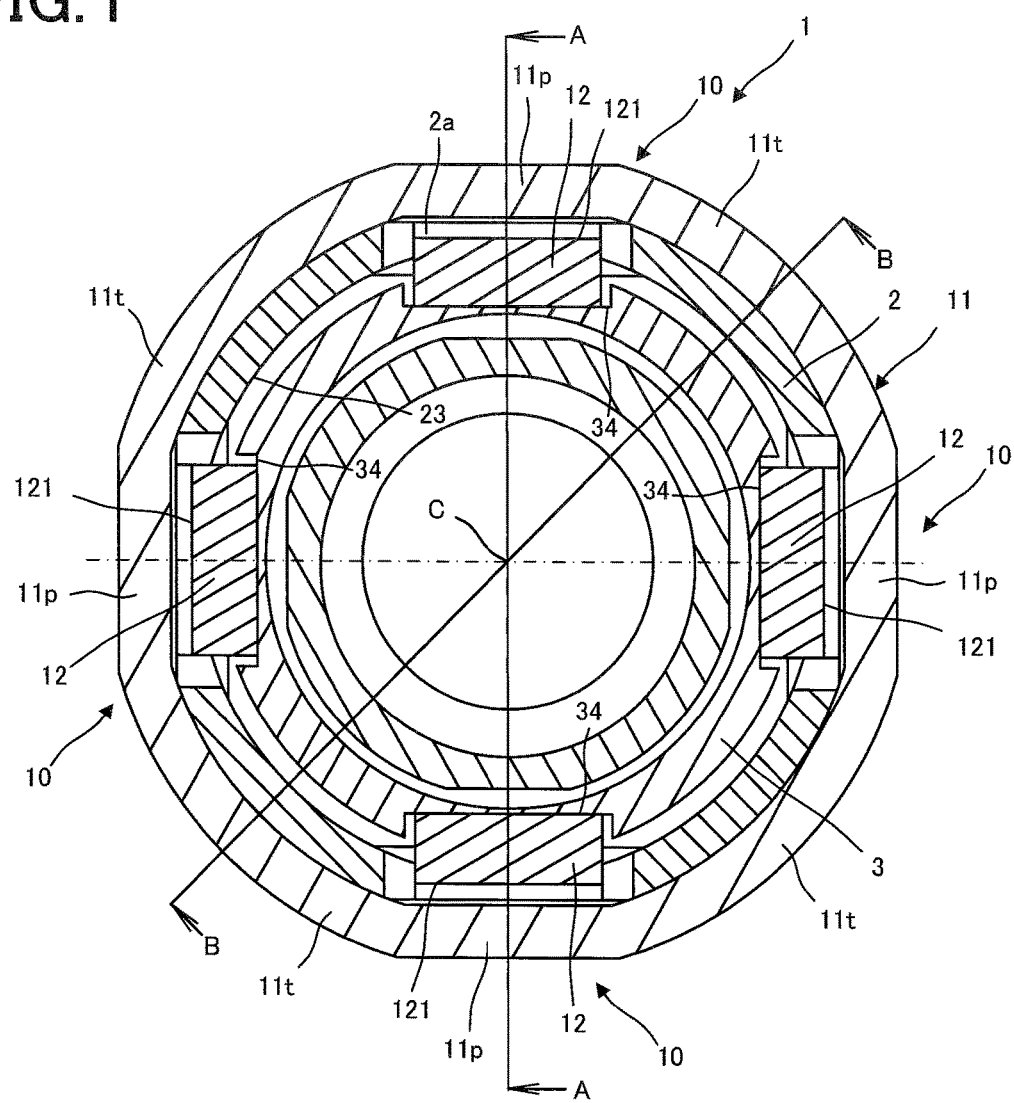
FIG. 1 is a sectional view of the driving unit according to one embodiment of the invention as taken orthogonally with respect to its axis.
Figure 2:
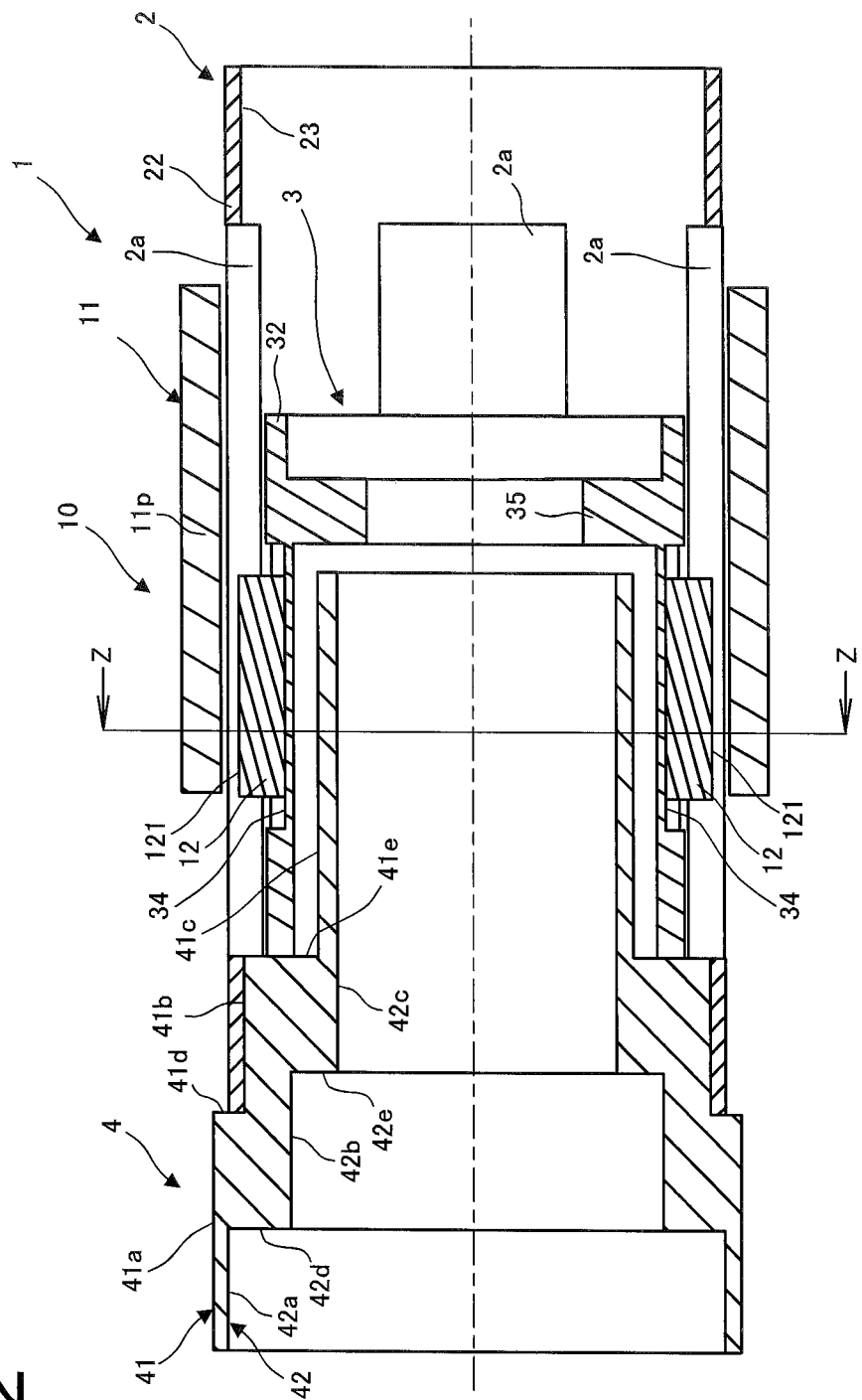
FIG. 2 is a sectional view of FIG. 1 as taken on section A-A.
Figure 3:
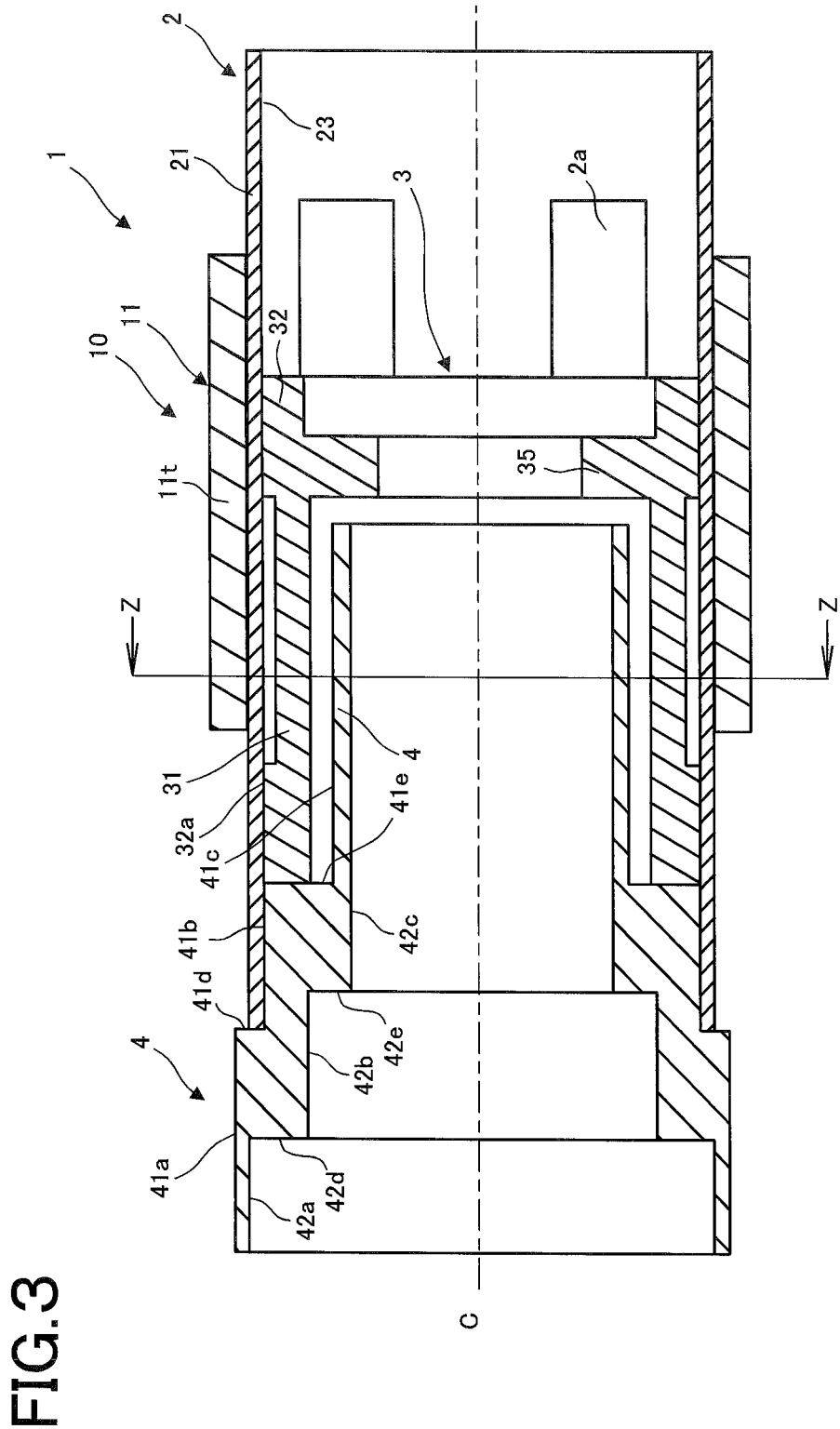
FIG. 3 is a sectional view of FIG. 1 as taken on section B-B.
Figure 4:
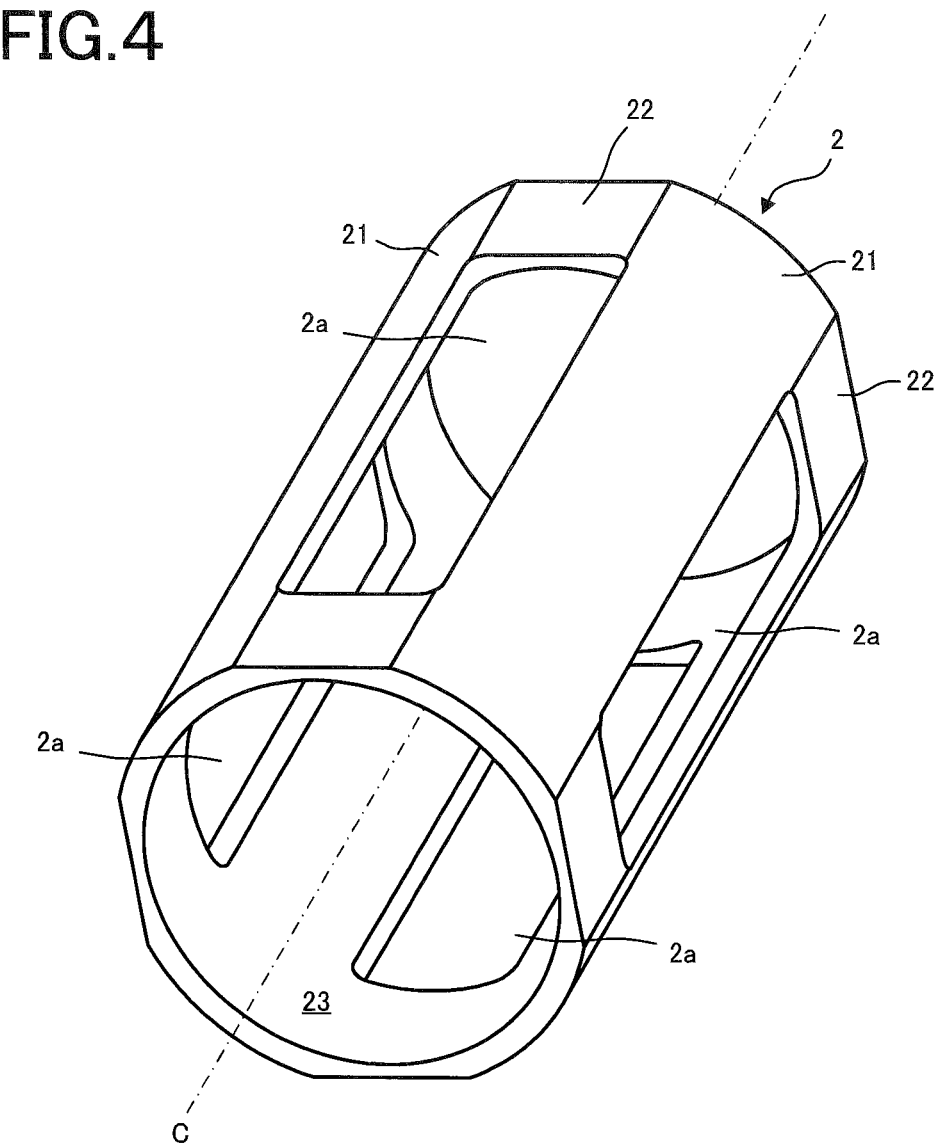
FIG. 4 is illustrative of the fixed part in the driving unit according to the first embodiment of the invention.
Figure 5:
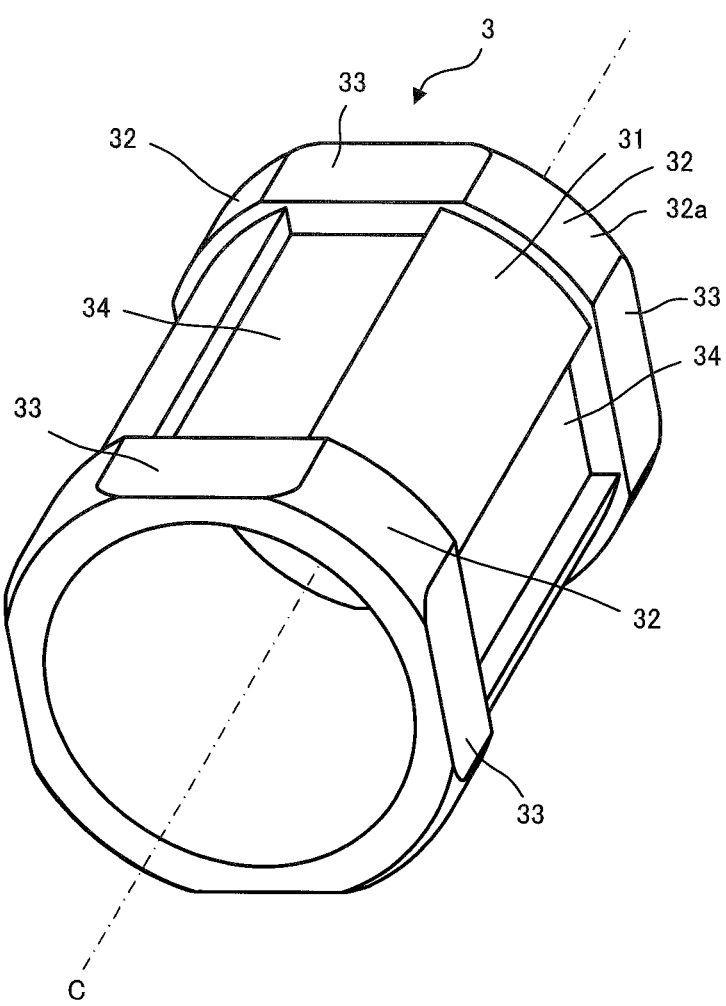
FIG. 5 is illustrative of the movable part in the driving unit according to the first embodiment of the invention.
Figure 6:
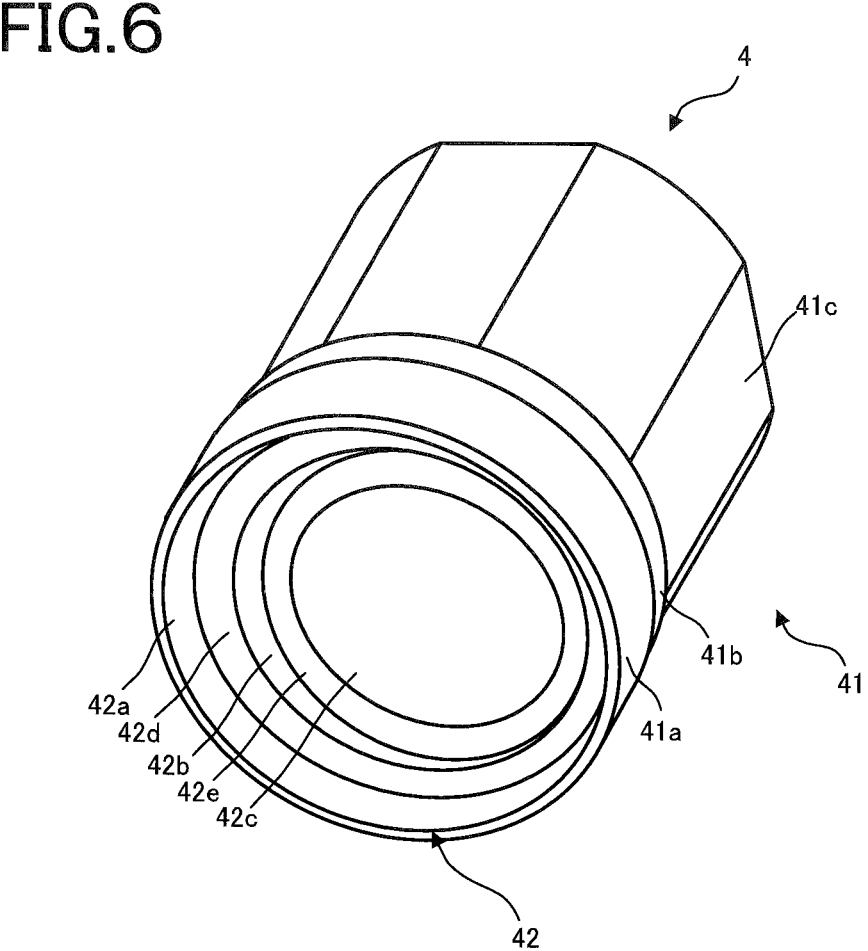
FIG. 6 is illustrative of the front frame part in the driving unit according to the first embodiment of the invention.
Figure 7:
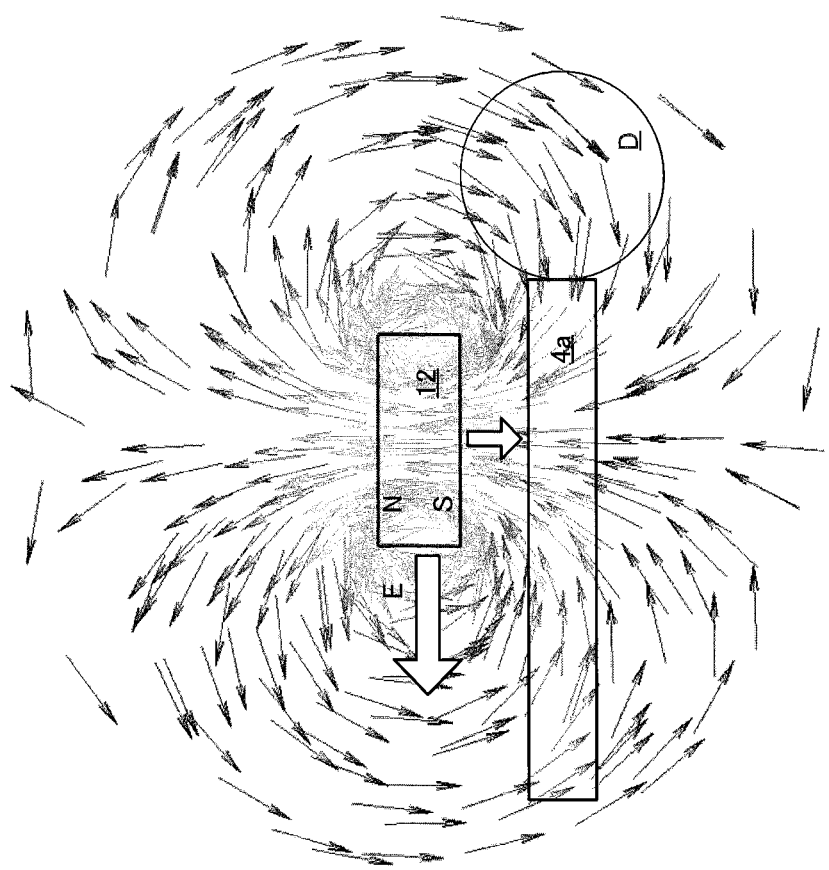
FIG. 7 is illustrative of an actuation state of the driving unit according to the first embodiment of the invention.

FIG. 1 is a sectional view of the driving unit according to the first embodiment of the invention as taken orthogonally with respect to its axis. FIG. 2 is a sectional view of FIG. 1 as taken on section A-A, and FIG. 3 is a sectional view of FIG. 1 as taken on section B-B. FIG. 4 is illustrative of the fixed part in the driving unit according to the embodiment described herein, and FIG. 5 is illustrative of the movable part in the driving unit according to the embodiment described herein. FIG. 6 is illustrative of the front frame part in the driving unit according to the embodiment described herein, and FIG. 7 is illustrative of a magnetic material in the driving unit according to the embodiment described herein. Note here that the sectional view of FIG. 1 is taken on section Z-Z in FIGS. 2 and 3.

The driving unit 1 according to the embodiment described herein includes a fixed part 2, a movable part 3 that is movable relative to the fixed part 2, a front frame part 4 attached to the fixed part 2, and a voice coil motor 10 adapted to generate a driving force for movement of the movable part 3 relative to the fixed part 2.

As shown in FIG. 4, the fixed part 2 includes a member having a tubular form with respect to a given axis C. The fixed part 2 according to the embodiment described herein includes a tubular member 21 and a planar portion 22 formed on a part of the outer circumference side of the tubular member 21. Note here that the inner circumference surface 23 of the tubular member 21 and planar portion 22 may be in a cylindrical shape. A part of the planar portion 22 is lightened as indicated by 2a. In the first embodiment described herein, there are four diametrically orthogonal planar portions 22 provided for each 90° with the axis C of the tubular member 21 as center. Each planar portion 22 includes a lightened site in the form of an opening 2a in a position except both its axial ends. Note here that the opening 2a may be formed in at least a part of the planar portion 22 or, alternatively, it may be formed in such a way as to protrude out of a part of the tubular member 21.

As shown in FIG. 5, the movable part 3 includes a member having a tubular form with respect to a given axis C. The movable part 3 according to the embodiment described herein includes a tubular member 31, protruding edges 32 formed at both ends of the tubular member 31 in the axis C direction of the tubular member 31 and having an outer diameter larger than the diameter of the tubular member 31, a planar portion 33 formed on a part of the outer circumference side of the protruding edge 32, a step portion 34 formed between the planar portions 33 at both the ends in the axis C direction and nearer to the inner circumference side of the tubular member 31, and a small inner-diameter portion 35 formed on one side of the axial direction and having an inner diameter smaller than the diameter of the inner circumference surface of the tubular member 31. The tubular member 31 and protruding edge 32 of the movable part 3 may be assembled of separate members.

In the embodiment described herein, there are four step portions 34 provided for each 90° with the axis C of the tubular member 31 as center, and the respective step portions 34 form a diametrically orthogonal plane for each 90° with respect to the center of the axis C.

The front frame part 4 is a tubular member including an outer circumference portion 41 and an inner circumference portion 42, and includes a magnetic material. The outer circumference portion 41 includes a first outer circumference component 41a, a second outer circumference component 41b, a third outer circumference component 41c, a first outer step component 41d and a second outer step component 41e. The inner circumference portion 42 includes a first inner circumference component 42a, a second inner circumference component 42b, a third inner circumference component 42c, a first inner step component 42d and a second inner step component 42e.

The first outer circumference component 41a is the diametrically largest of the outer circumference portion 41, and the third outer circumference component 41c is the diametrically smallest of the outer circumference portion 41. The second outer circumference component 41b has a length halfway between the lengths of the first 41a and the third outer circumference component 41c. There is the first outer step component 41d formed between the first 41a and the second outer circumference component 41b, and there is the second outer step component 41e formed between the second 41b and the third outer circumference component 41c.

The first inner circumference component 42a is the diametrically largest of the inner circumference portion 42, and the third inner circumference component 42c is the diametrically smallest of the inner circumference portion 42. The second inner circumference component 42b has a length halfway between the lengths of the first 42a and the third inner circumference component 42c. There is the first inner step component 42d formed between the first 42a and the second inner circumference component 42b, and there is the second inner step component 42e formed between the second 42b and the third inner circumference component 42c.

The front frame part 4 includes a magnetic material having a relative magnetic permeability of 1.0001 or greater. In the embodiment described herein, while the front frame part 4 is formed entirely of austenite stainless steel, it is to be noted that the front frame part 4 may be formed partly of a magnetic material. Alternatively, a material having a low relative magnetic permeability such as copper, silver or lead may be nickel-plated or otherwise treated in such a way as to have a relative magnetic permeability of 1.0001 or greater.

As shown in FIGS. 2 and 3, the voice coil motor 10 includes a coil 11 located on the fixed part 2 and a magnet 12 mounted on the movable part 3 in such a way as to be opposite to the coil 11.

As shown in FIG. 2, the coil 11 in the embodiment described herein is wound around the outer circumference of the fixed part 2. The coil 11 includes a plane 11p corresponding to the opening 2a in the fixed part 2; that is, the coil 11 has an arrangement wherein the planar portion 11p and cylindrical portion 11t are alternately located in the circumferential direction.

As shown in FIG. 2, the magnets 12 are located at the step portion 34 of the movable part 3 for each 90° with respect of the center of the axis in such a way as to be opposite to the planar portions 11p of the coil 11. It is thus possible to place the magnets 12 in a stable manner so that a stable magnetic field can be created so as to prevent any shake of the movable part 3 that are moving relative to the fixed part 2. The magnet 12 is diametrically magnetized; for instance, the side of the magnet 12 facing the coil 11 may be magnetized as an N-pole and the opposite side as an S-pole.

In the driving unit 1 according to the embodiment described herein, the movable part 3 having the magnet 12 in opposition to the coil 11 is located on the inner circumference side of the fixed part 2 having the coil 11 wound around. Accordingly, the planar portion 11p of the coil 11 comes to lie in a magnetic field in a direction orthogonal to the diametrically outer surface 121 of the magnet 12; so it is possible to boost up driving efficiency and move the movable part 3 rapidly. Further, the driving unit 1 is easier to assemble because the diametrically outer surface 121 of the magnet 12 is formed of a plane.

The axial width of the coil 11 is preferably greater than the axial width of the magnet 12 such that the magnet 12 always lies within the axial width of the coil 11 in the moving range of the movable part 3.

With the magnet 12 placed at the movable part 3, the diametrically outer surface 121 of the magnet 12 is located in the opening 2a in the fixed part 2, as shown in FIGS. 2 and 3. That is, a first distance from the axis C to the diametrically outer surface 121 of the magnet 12 is longer than a second distance from the axis C to the inner circumference surface 23 of the fixed part 2. Because the first distance is longer than the second distance, the diameter of the fixed part 2 can be smaller and, hence, the size and weight of the driving unit 1 can be smaller. It is consequently possible to boost up the driving efficiency of the driving unit 1 and move the movable part 3 rapidly.

As shown in FIG. 3, the outer circumference surface of the protruding edge 32 in the movable part 3 forms a sliding surface 32a in contact with the inner circumference surface 23 of the fixed part 2. Contact of the inner circumference surface 23 of the fixed part 2 with the sliding surface 32a of the movable part 3 allows for movement of the movable part 3 while it comes constantly in contact with the fixed part 2.

In turn, this prevents tilting of the movable part 3 relative to the fixed part 2, making sure unerring movement of the movable part 3.

Further, it is preferable that the driving unit 1 is formed symmetrically with respect to the axis C. The structure allowing for contact of the inner circumference surface 23 of the fixed part 2 with the sliding surface 32a of the movable part 3 is combined with the symmetrical configuration of the whole driving unit 1 with respect to the axis C so that the center of gravity can be positioned on the axis C, contributing to further prevention of tilting of the movable part 3 relative to the fixed part 2. In other words, it is possible to maintain parallelism upon abutment of the movable part 3 against the fixed part 2.

While the magnets 12 are placed for each 90° with the axis C as center in the first embodiment, it is to be understood that they may be placed at any desired angles other than 90°.

The front frame part 4 is inserted over one end of the fixed part 2 such that the third outer circumference component 41c is located inside the inner circumference surface of the movable part 3, and the second outer circumference component 41b is inserted while coming in contact with the inner circumference surface 23 of the fixed part 2 until the one end of the fixed part 2 is in contact with the first outer step component 41d.

FIG. 7 is a schematic view of a magnetic material located in a magnetic field generated by a magnet.

In the embodiment described herein, a magnet 12 is magnetized in a direction orthogonal to the axis C. In FIG. 7, the magnetic field generated by the magnet 12 is indicated by arrows directing from the N-pole to the S-pole of the magnet 12. Located the magnetic material 4a in the magnetizing direction of the magnet 12, the magnetic material 4a generates a magnetic force in proportion to the square of a magnetic flux density and the surface area of the magnet 12.

In the embodiment described herein, the magnet 12 and magnetic material 4a are displaced in the axis C direction; so a vector component in an area D shown in FIG. 7 will not affect the magnetic material 4a. Accordingly, the magnetic force applied to the magnetic material 4a is thrown off balance, resulting in the generation of a biasing force. In the embodiment described herein, there is a biasing force acting on the magnet 12 in a direction indicated by an action arrow E because the front frame part 4 is attached to the fixed part 2 and the magnet 12 is placed on the movable part 3. In other words, the biasing force acts in such a direction as to bring the movable part 3 in contact with the second outer step 41e.

Figure 8:
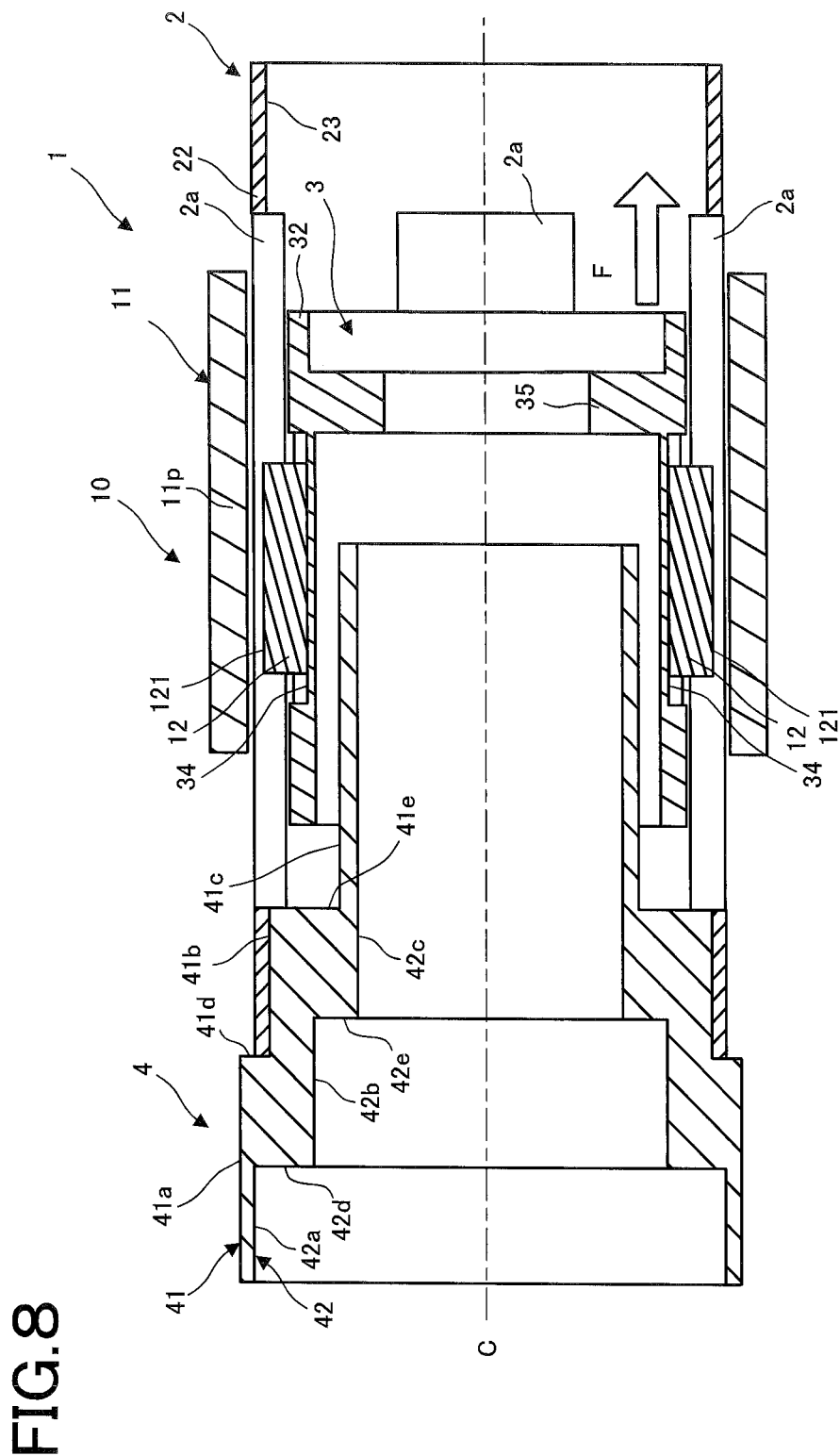
FIG. 8 is illustrative of an actuation state of the driving unit according to one embodiment of the invention.

FIG. 8 is illustrative of the actuation state of the driving unit according to the embodiment described herein.

Upon the passage of electric current through the coil 11 in the driving unit 1, an axial force is generated in the movable part 3 under the influence of the magnetic field of the magnet 12 with the result that the movable part 3 moves in a direction indicated by an action arrow F relative to the fixed part 2. For instance, electric current through the coil 11 may be controlled such that the movable part 3 moves from the position indicated in FIG. 2 to the position indicated in FIG. 8 relative to the fixed part 2. Note here that even while the movable part 3 is moving, the diametrically outer surface of the magnet 12 remains located within the opening 2a in the fixed part 2.

As the electric current flowing through the coil 11 is then cut off, it urges the movable part 3 to go back to the state of FIG. 2 for the reason shown in FIG. 7. In the state of FIG. 2, the biasing force acts on the magnet 12 so that the electric current flowing through the coil 11 can be curtailed or absented, alternatively, the movable part 2 can be held in a position in contact with the second upper step component 41e.

Thus, the driving unit 1 according to the embodiment described herein can be reduced in terms of size and weight, and improved driving efficiency allows for rapid movement of the movable part 3. Even during actuation, the inner circumference surface 23 of the fixed part 2 comes into contact with the sliding surface 32a of the movable part 3 so that tilting of the movable part 3 relative to the fixed part 2 can be held back for unerring movement of the movable part 3. Further, the biasing force generated by the magnet 12 for the magnetic material 4a makes it possible to take unerring hold of the movable part 3.

Figure 9:
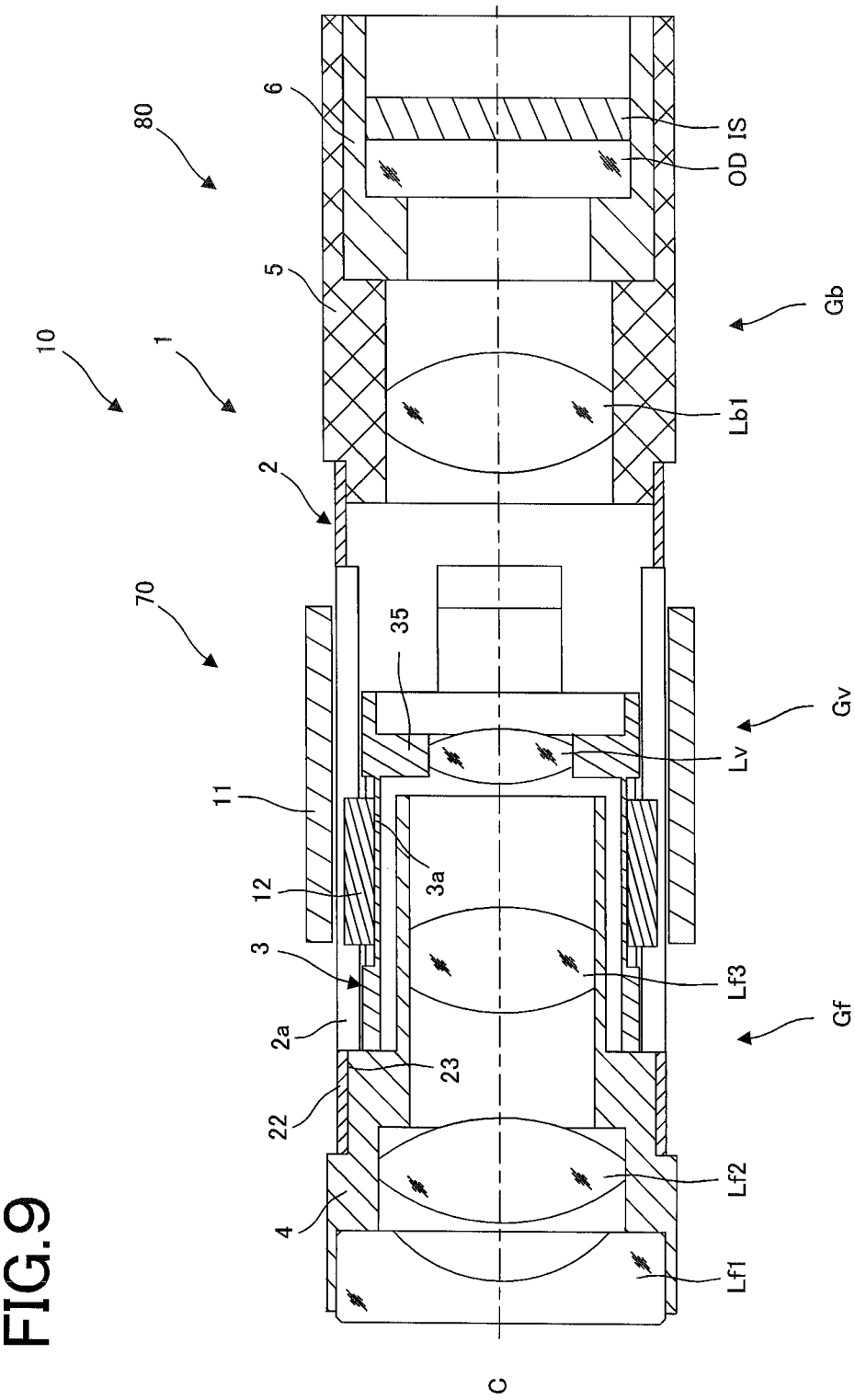
FIG. 9 is illustrative in section of the optical unit and imaging apparatus according to one embodiment of the invention.

FIG. 9 is illustrative of the optical unit 70 and imaging apparatus 80 according to one embodiment of the invention.

The optical unit 70 includes a driving unit 1 similar to that according to the first embodiment, a front lens group Gf attached to the front frame part 4 of the driving unit 1, and a moving lens group Gv attached to a smaller-diameter portion 35 of the movable part 3.

The front lens group Gf includes a first front lens Lf1 attached to the first inner circumference component 42a, a second front lens Lf2 attached to the second inner circumference component 42b, and a third front lens Lf3 attached to the third inner circumference component 42c. The moving lens group Gv includes a moving lens Lv. Preferably, the center axis of each lens is the same as the axis C of the driving unit 1.

The optical unit 70 is designed such that with the moving lens Lv attached to the moving lens group Gv, the movable part 3 is movable relative to the fixed part 2 in the axis C direction. Movement of the movable part 3 relative to the fixed part 2 permits for movement of the focal position of the optical unit 70.

The imaging apparatus 80 includes the optical unit 70, a back lens group Gb attached to the back frame part 5 of the fixed part 2 on the image side of the optical unit 70, and an imaging device IS attached to an imaging device frame 6 with a light-receiving portion located on an image plane. Note here that the back frame part 5 may be integrally formed with the imaging device frame 6.

In the embodiment described herein, the back lens group Gb includes a first back lens Lb1 held by the back frame part 5 attached to the fixed part 2 as by press fitting or bonding. In the embodiment described herein, the imaging device IS includes any type of image sensor such as CCD or CMOS, and is held in the imaging device frame 6. On the object side of the imaging device IS, a filter or cover glass or other optical devices OD are located in adjoining relations.

It is here to be appreciated that the lens arrangement of the front lens group Gf, back lens group Gb and moving lens group Gv is not limited to the aforesaid one; it may be modified as required. In the embodiment described herein, the front frame part 4 and the back frame part 5 are bonded to the fixed part 2 and the imaging device frame 6 is held in the back frame part 5 as mentioned above; however, one or more of these frames may be collectively taken as a part of the fixed part.

Referring to the imaging apparatus 80 according to the embodiment described herein, it is when the movable part 3 is positioned on the most image side of the movable range that the imaging magnification gets highest, and it is when the movable part 3 is positioned on the most object side that the imaging magnification becomes lowest. To put it another way, it is when the movable part 3 is positioned on the most image side of the movable range that the focal length gets longest and there is a telephoto end state created with a narrow field of view, and it is when the movable part 3 is positioned on the most object side of the movable range that the focal length gets shortest and there is a wide-angle end state created with a wide field of view.

Thus, reductions in the size and weight of the driving unit 1 permit for reductions in the size and weight of the imaging apparatus 80, and movement of the movable part 3 relative to the fixed part 2 permits for rapid zoom change of the imaging apparatus 80.

Incidentally, such imaging apparatus 80 as described above may be used with an electronic camera apparatus, especially a digital camera or a video camera, as embodied just below.

Figure 10:
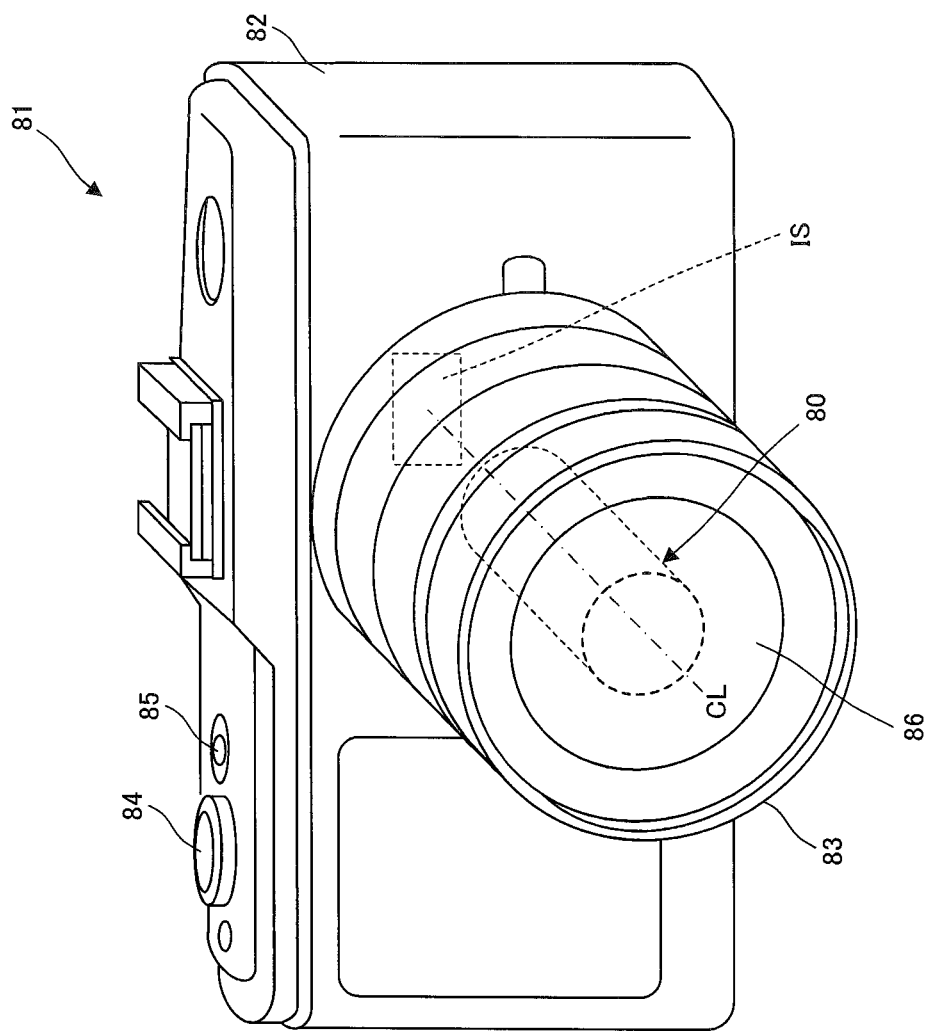
FIG. 10 is illustrative of one example of a digital camera including the imaging apparatus according to one embodiment of the invention.

FIG. 10 is illustrative of one example of the digital camera 81 including the imaging apparatus 80 according to the embodiment described herein.

The imaging apparatus 80 may be used with some products such as a digital camera 81, a digital video camera, and a cellular phone. An example of application of the imaging apparatus 80 according to the embodiment described herein to the digital camera 81 is now explained.

As depicted in FIG. 10, the digital camera 81 according to the embodiment described herein includes a camera body 82, and a lens barrel 83 in the form of an interchangeable lens. Note here that the camera body 82 may be detachable from, or integral with, the lens barrel 83.

In the camera body 82, there is an imaging device IS mounted for electronic taking and recording of subject images. On the light-receiving site of the imaging device IS, there are multiple elements arranged in a planar array to produce out electric signals in response to incident light at a given timing. The lens barrel 83 is provided with a plurality of objective lenses 86 along the direction of an optical axis CL, and includes the optical unit 70 shown in FIG. 9. That is, the camera body 82 and a part of the lens barrel 83 make up the imaging apparatus 80. Note here that the front lens group Gf shown in FIG. 9 may be mounted in the lens barrel 83, and the optical unit 70 and back lens group Gb shown in FIG. 9 may be mounted in the camera body 82.

Mounted on the upper portion of the camera body 82 are a release switch 84 through which a camera operator enters an imaging instruction in it, and a power source switch 85 through which the camera operator turns on or off the camera body 82.

In the embodiment described herein, the release switch 84 is a push-button switch. Upon a semi-depression of the release switch 84, the imaging apparatus 80 is actuated for autofocus or the like and upon transition from the semi-depression to a full-depression of the release switch 84, the imaging apparatus 80 is actuated for imaging and recording of images. Note here that a touch-sensor switch or the like may be used in place of the push-button release switch 84.

Mounted on the back surface of the camera (not shown) are an image display unit, a zooming operation instruction portion for giving a zooming instruction to the imaging apparatus 80, etc. Mounted in the camera body 82 are a battery space for storing a primary or secondary battery for power supply and a recording medium space for storing a flash memory adapted to record images.

Figure 11:
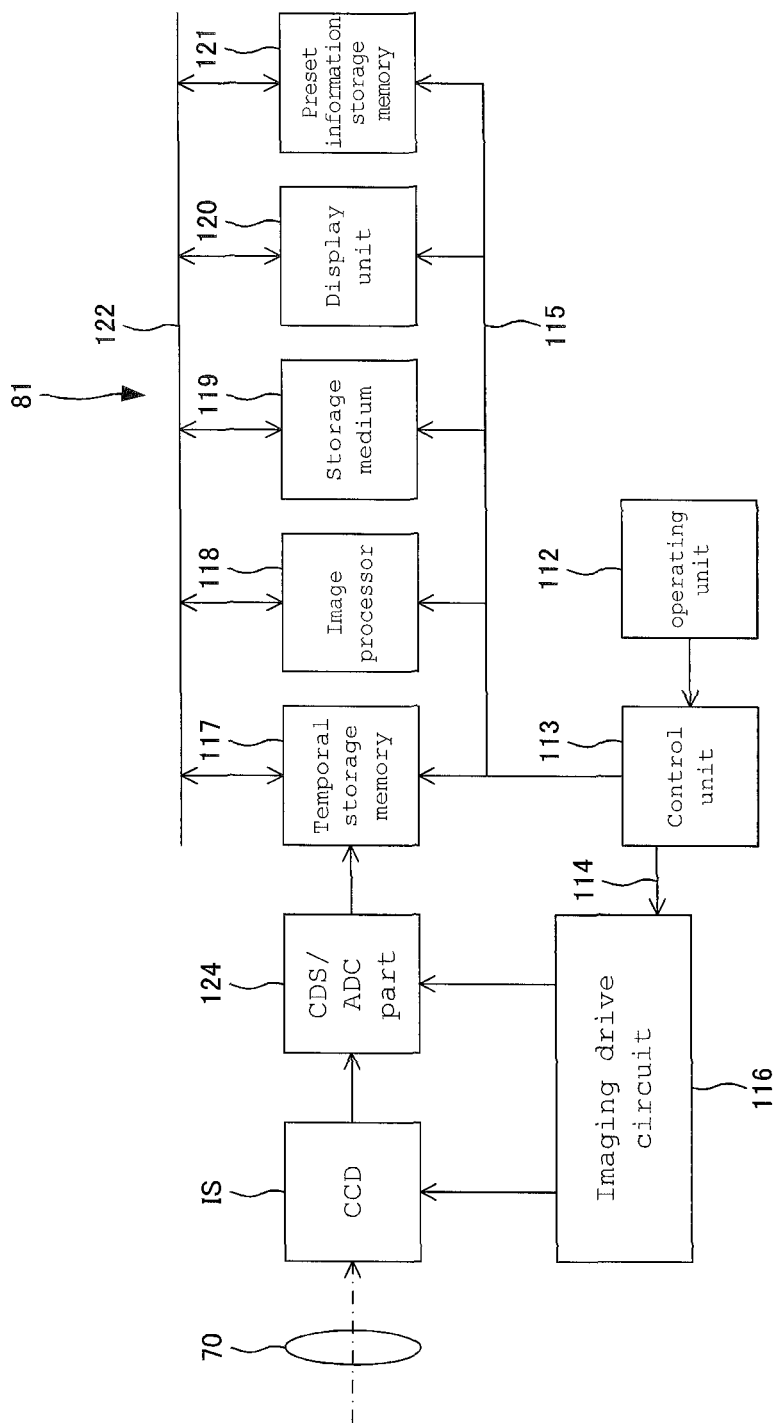
FIG. 11 is a block diagram for the internal circuitry of a main part of the digital camera according to one embodiment of the invention.

FIG. 11 is a block diagram for the internal circuitry of a main part of the digital camera 80 according to the embodiment described herein. Note here that in what follows, the processing means is made up of, for instance, a CDS/ADC 124, a temporal storage memory 117, and an image processor 118, and a storage means is made up of a memory medium, etc.

As can be seen from FIG. 11, the digital camera 81 includes an operating unit 112, a control unit 113 connected to the operating unit 112, an imaging drive circuit 116/temporal storage memory 117, an image processor 118, a memory medium 119, a display unit 120 and a preset information storage memory 121, connected to the control signal output port of the control unit 113 by way of buses 114 and 115.

The abovementioned temporal storage memory 117, image processor 118, storage medium 119, display unit 120 and preset information storage memory 121 are designed such that data are mutually entered and produced out by way of a bus 122, and the imaging drive circuit 116 is connected with the imaging device IS and CDS/ADC 124.

The operating unit 112 includes various input buttons or switches, and event information entered from outside (by the camera operator) by way of them is notified to the control unit 113. The control unit 113 is typically a central processing unit (CPU) or the like, and includes a program memory (not shown) inside so that the digital camera 81 is controlled on its entirety according to the program stored in the program memory.

The imaging device IS such as CCD is driven and controlled by the imaging drive circuit 116 to convert the quantity of light per pixel of an object image formed via the optical unit 70 into an electric signal that is then produced out to the CDS/ADC 124.

The CDS/ADC 124 is a circuit in which the electric signals entered through the imaging device IS are amplified and subjected to analog-to-digital conversion to produce the image raw data (Bayer data hereinafter called the RAW data) subjected to only amplification/digital conversion processing out to the temporal storage memory 117.

The temporal storage memory 117 is a buffer including an SDRAM as an example or a memory device adapted to temporarily store the RAW data produced out from the CDS/ADC 124. The image processor 118 is a circuit adapted to read out the RAW data stored in the temporal storage memory 117 or the RAW data stored in the storage medium 119 thereby electrically implementing a variety of image processing steps including distortion correction based on image quality parameters designated by the control unit 113.

The storage medium 119 includes a detachably mounted card or stick type storage medium including flash memories as an example, and the RAW data transferred from the temporal storage memory 117 or the image data processed by the image processor 118 are recorded and retained in these flash memories.

The display unit 120 is made up of a liquid crystal monitor so as to display the RAW data taken, image date, operation menus, etc. The preset information storage memory 121 includes a ROM having a variety of image quality parameters stored beforehand, and a RAM adapted to store image quality parameters read out from the ROM by the input operation of the operating unit 112.

The digital camera 81 assembled in this way, because of incorporating the optical unit 70 according to the embodiment described herein, ensures that the imaging apparatus 80 is of smaller size and well compatible with the taking of moving images.

Figure 12:
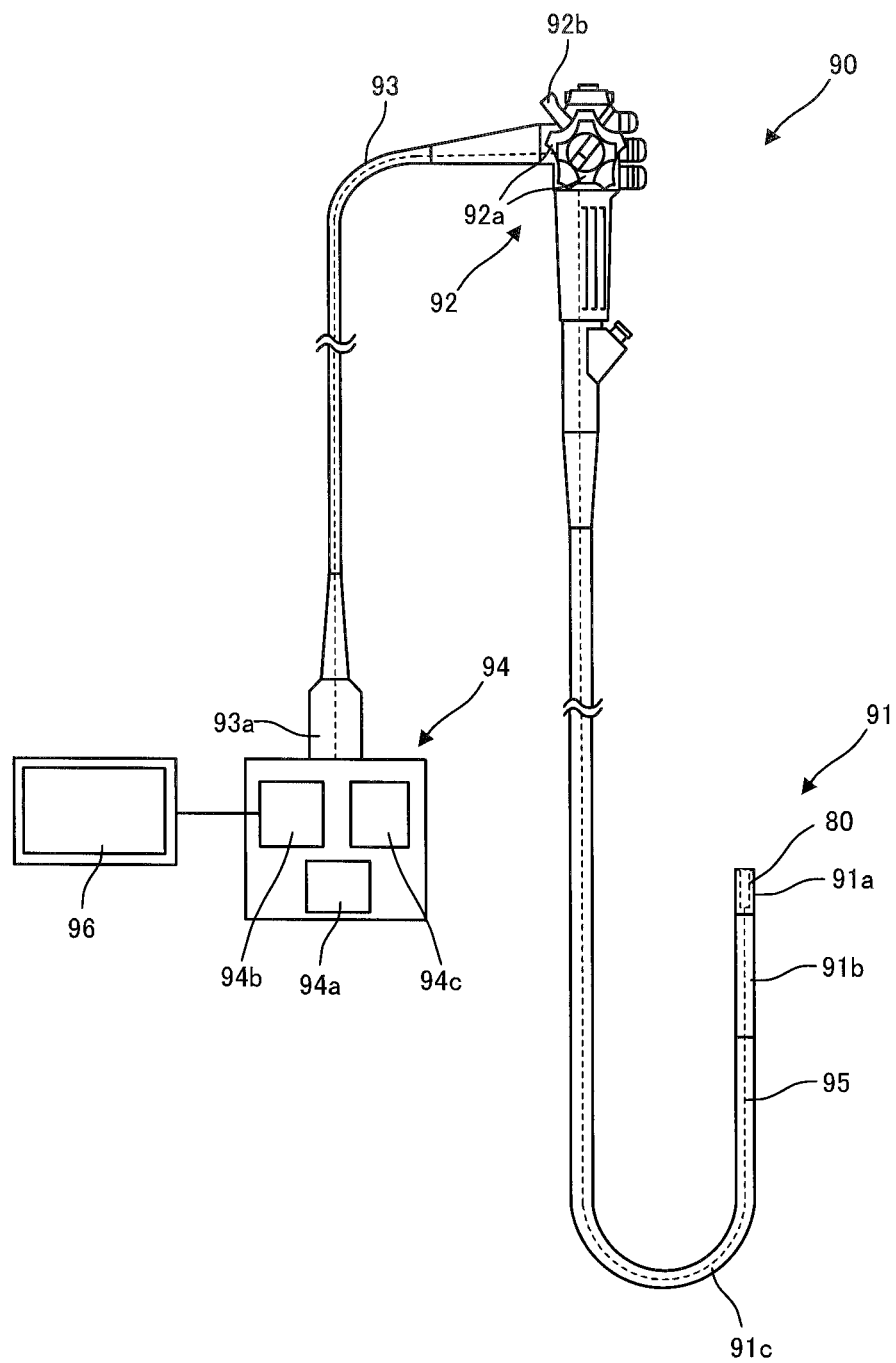
FIG. 12 is illustrative of one example of the endoscope including the imaging apparatus according to one embodiment of the invention.

FIG. 12 is illustrative of one example of the endoscope 90 including the imaging apparatus 80 according to the embodiment described herein.

The endoscope 90 according to the embodiment described herein is capable of insertion through a subject of interest such as the human body for optical taking of a given site of interest in the subject. Note here that the subject through which the endoscope 90 is to be inserted may be living bodies inclusive of the human body as well as artifacts such as machinery and structures.

The endoscope 90 includes an insert part 91 inserted through the interior of the subject of interest, an operating unit 92 positioned at the proximal end of the insert part 91 and a universal cable 93 that is a composite cable extended out from the operating unit 92.

The insert part 91 includes a distal-end portion 91a attached to the distal end, a curving portion 91b located on the proximal end side of the distal-end portion 91a and a flexible tubular portion 91c located on the proximal end side of the curving portion 91b and connected to the distal end side of the operating unit 92. The distal-end portion 91a has the imaging apparatus 80 (shown in FIG. 9) built inside. Note here that the endoscope 90 used may be a hard one having no flexible tubular portion 91c in the insert part 91.

The operating unit 92 includes an angle operating portion 92a for operation of the curving state of the curving portion 91b and a zoom operating portion 92b for giving an instruction to the voice coil motor 10 (shown in FIG. 9) to implement zoom operation of the imaging apparatus 80. The angle operating portion 92a has a knob form and the zoom operating portion 92b has a lever form; however, they may each be configured as a volume switch, a push switch or the like.

The universal cord 93 is a member for connecting the operating unit 92 to external hardware 94 by way of a connector 93a. The external hardware 94 includes a driving control portion 94a for controlling the curving state of the curving portion 91b, an image control portion 94b for controlling the imaging apparatus 80, a light source control portion 94c for controlling a light source (not shown), and the like.

A cable 95 such as a wire, an electric wire, an optical fiber or the like is inserted through the insert part 91, operating unit 92 and universal cord 93. The wire is provided so as to connect the driving control portion 94a located in the external hardware 94 to the operating unit 92 and curving portion 91b, the electric wire is provided for making electric connections between the imaging apparatus 80 and the operating unit 92 and image control portion 94b, and the optical fiber is provided for making optical connections between the light source and the operating unit 92 and light source control portion 94c.

The driving control portion 94a is built up of an actuator or the like to move the wire advanceably and retractably for control of the curving state of the curving portion 91b. The image control portion 94b implements driving control of the voice coil motor 10 built in the imaging apparatus 80 shown in FIG. 9 and processing of images taken through the imaging device IS. The images processed by the image control portion 94b appear on an image display 96. The light source control portion 94c is provided so as to control the brightness of the source of light exiting out from the distal-end portion 91a, and so on.

It is here to be appreciated that the operating unit 92 and external hardware 94 may be formed separately from the insert part 91 for remote operation and control of the insert part 91.

The endoscope 90 assembled in this way, because of incorporating the imaging apparatus 80 according to the embodiment described herein, ensures that it is of smaller size and well compatible with quick zoom change and the taking of moving images.

According to one embodiment of the invention, it is thus possible to provide a driving unit 1 including a tubular fixed part 2 with a given axis C as center, a tubular movable part 3 located inside the fixed part 2 with the axis C as center, a front frame part 4 attached to one end side of the fixed part 2 and including at least a magnetic material, and a voice coil motor 10 that is capable of moving the movable part 3 relatively with respect to the fixed part 2 in the axis C direction by a coil 11 located in the fixed part 2 and a magnet 12 located in the movable part 3, wherein the magnet 12 in the movable part 3 is biased by the magnetic material. It is thus possible to provide the driving unit 1 in which the voice coil motor is used for advanceable and retractable movement of the movable part relative to the fixed part, and which uses a simple structure to generate a biasing force and results in size and weight reductions.

According to one embodiment of the invention, the magnet 12 is located on the outer circumference side of the movable part 3 and at least a portion of the front frame part 4 is located on the inner circumference side of the movable part 3. It is thus possible to achieve further reductions in the size and weight of the driving unit 1.

According to one embodiment of the invention, it is possible to achieve further reductions in the size and weight of the driving unit 1 because at least a portion of the magnetic material is located on the inner circumference side of the movable part 3.

According to one embodiment of the invention, it is possible to achieve further reductions in the size and weight of the driving unit 1 because the front frame part 4 is formed of a magnetic material.

According to one embodiment of the invention, it is possible to provide the driving unit 1 that is capable of unerringly biasing the movable part 3 because the magnetic material has a permeability of 1.0001 or greater.

According to one embodiment of the invention, it is possible to provide the optical unit 70 wherein the movable part 3 is moved relative to the fixed part 2 for movement of its focal position, because it has the moving lens group Gv attached to the movable part 3 of the driving unit 1.

According to one embodiment of the invention, it is possible to provide the optical unit 70 of higher performance because it has the front lens group Gf attached to the front frame part 4.

According to one embodiment of the invention, it is possible to provide the imaging apparatus 80 that is reduced in terms of both size and weight and capable of rapid zoom change, because it includes the optical unit 70 and the back frame part 5 attached to other end side of the fixed part 2, wherein the back frame part 5 includes the back lens group Gb on which light passing through the moving lens group Gv is incident and the imaging device IS on which light passing through the back lens group Gb is incident.

According to one embodiment of the invention, it is possible to provide the endoscope 90 that is of smaller size, capable of rapid zoom change, and well compatible with the taking of moving images because it includes the imaging apparatus 80.

With the endoscope 90 according to one embodiment of the invention, the movable part 3 is biased toward the front frame part 4 side so that an area over a wide range can be imaged in focus on the wide-angle side in a normal mode and focus is placed on the telephoto side for magnification at the time of viewing, treatments or the like in order to be compatible with applications.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Driving unit
2: Fixed part
3: Movable part
4: Front frame part
5: Back frame part
6: Imaging device frame (back frame part)
10: Voice coil motor
11: Coil
12: Magnet

The invention claimed is:

1. A driving unit comprising:
a tubular fixed part extending along a longitudinal axis, the longitudinal axis being positioned at a center of the fixed part,
a movable part located inside the fixed part, the movable part being movable along a longitudinal axis direction,
a front frame part attached to one end side of the fixed part, at least a portion of the front frame part being formed of a magnetic material, at least a portion of the front frame part being located on an inner circumference of the movable part, and
a voice coil motor capable of moving the movable part relatively with respect to the fixed part in the longitudinal axis direction, the voice coil motor including a coil wound around an outer circumference of the fixed part and a magnet located on an outer circumference of the movable part,
wherein the magnet in the movable part opposes the coil in a direction orthogonal to the longitudinal axis direction, the magnet and the magnetic material being offset in the longitudinal direction such that the magnet is biased by the magnetic material.

2. The driving unit according to claim 1, wherein the front frame part comprises the magnetic material.

3. The driving unit according to claim 1, wherein the magnetic material has a permeability of 1.0001 or greater.

4. The driving unit according to claim 1, wherein a first distance from the longitudinal axis to a diametrically outer surface of the magnet of the movable part is longer than a second distance from the longitudinal axis to an inner circumference surface of the fixed part.

5. An optical unit comprising a moving lens group attached to the movable part in the driving unit according to claim 1.

6. The optical unit according to claim 5, further comprising a front lens group attached to the front frame part.

7. An imaging apparatus comprising:
the optical unit of claim 5; and
a back frame part attached to an other end side of the fixed part,
wherein the back frame part includes a back lens group on which light passing through the moving lens group is incident, and
an imaging device on which light passing through the back lens group is incident.

8. An endoscope comprising the imaging apparatus according to claim 7.

9. The endoscope according to claim 8, wherein the movable part is biased toward a front frame part side.

* * * * *